(12) United States Patent
Kube (10) Patent No.: US 10,203,261 B2
(45) Date of Patent: Feb. 12, 2019

(54) FLUID MEASURING DEVICE AND MEASURING HEAD DEVICE FOR MOISTURE DETECTION, IN PARTICULAR IN CONTAINERS FOR FLUID-SENSITIVE ELECTRICAL AND/OR ELECTRONIC COMPONENTS IN ROAD VEHICLES

(71) Applicant: VOLKSWAGEN AKTIENGESELLSCHAFT, Wolfsburg (DE)

(72) Inventor: Roland Kube, Schwuelper (DE)

(73) Assignee: Volkswagen Aktiengesellschaft, Wolfsburg (DE)

( * ) Notice: Subject to any disclaimer, the term of this patent is extended or adjusted under 35 U.S.C. 154(b) by 10 days.

(21) Appl. No.: 15/651,153

(22) Filed: Jul. 17, 2017

(65) Prior Publication Data
US 2018/0017462 A1   Jan. 18, 2018

(30) Foreign Application Priority Data
Jul. 15, 2016 (DE) .......................... 10 2016 212 986

(51) Int. Cl.
*G01M 3/18* (2006.01)
*F42B 35/00* (2006.01)
(Continued)

(52) U.S. Cl.
CPC ............. *G01M 3/186* (2013.01); *F42B 35/00* (2013.01); *G01M 3/025* (2013.01);
(Continued)

(58) Field of Classification Search
CPC ...... G01M 3/186; G01M 3/3245; H05K 5/06; G01N 27/221; G01N 27/223; F42B 35/00; F21V 31/005
See application file for complete search history.

(56) References Cited

U.S. PATENT DOCUMENTS 4,227,151 A * 10/1980 Ellis ...................... D06F 39/004
324/441
4,266,188 A * 5/1981 Thompson ............. G01R 27/22
324/606
(Continued)

FOREIGN PATENT DOCUMENTS

CN   201724710 U   1/2011
DE   2837102 A1   3/1979
(Continued)

*Primary Examiner* — An T Nguyen
(74) *Attorney, Agent, or Firm* — Laurence A. Greenberg; Werner H. Stemer; Ralph E. Locher (57) ABSTRACT

A fluid measuring device includes a measuring head device having a measuring head with separated and electrically insulated electrodes and measuring head contacts each connected to a respective electrode. A measuring circuit includes terminal contacts each connected to a respective measuring head contact. The measuring circuit includes a current source for pulsed energizing of the measuring head connected to the terminal contacts. The measuring circuit includes an output circuit between the terminal contacts including a measuring capacitor and an evaluation circuit ascertaining state-of-charge information regarding the measuring capacitor. A supplementary circuit in the measuring head is connected to the measuring head contacts and establishes basic capacitance and resistance properties therebetween corresponding to capacitance and resistance properties between the measuring head contacts upon contact with predefined partial wetting of the electrodes by conductive fluid having predefined conductivity without the supplementary circuit. A measuring head device is also provided.

9 Claims, 8 Drawing Sheets

(51) Int. Cl.
*G01M 3/32* (2006.01)
*G01N 27/22* (2006.01)
*H05K 5/06* (2006.01)
*G01M 3/02* (2006.01)
*F21V 31/00* (2006.01)

(52) U.S. Cl.
CPC ........ *G01M 3/3245* (2013.01); *G01N 27/223* (2013.01); *H05K 5/06* (2013.01); *F21V 31/005* (2013.01)

(56) References Cited

U.S. PATENT DOCUMENTS

| | | | |
|---|---|---|---|
| 5,455,513 A | 10/1995 | Brown et al. | |
| 5,483,172 A | 1/1996 | Radford | |
| 8,865,333 B2 | 10/2014 | Phlegm et al. | |
| 9,096,134 B2 | 8/2015 | Namou et al. | |
| 9,217,690 B2 | 12/2015 | Skelton et al. | |
| 9,804,113 B2 * | 10/2017 | Kumaran | G01N 27/223 |
| 2003/0183001 A1 * | 10/2003 | Zimmermann | G01F 15/022 |
| | | | 73/295 |
| 2007/0079653 A1 * | 4/2007 | Zuleta | G01F 23/243 |
| | | | 73/304 R |
| 2009/0139324 A1 * | 6/2009 | Morimoto | A47J 27/212 |
| | | | 73/292 |
| 2013/0031963 A1 * | 2/2013 | Ritchie, Jr. | G01N 33/2847 |
| | | | 73/61.43 |
| 2013/0214797 A1 * | 8/2013 | Gruden | D06F 39/004 |
| | | | 324/663 |
| 2014/0015511 A1 | 1/2014 | Matthe et al. | |
| 2015/0330932 A1 * | 11/2015 | Kumaran | G01N 27/223 |
| | | | 324/664 |
| 2016/0260312 A1 * | 9/2016 | Hazzard | G08B 21/20 |
| 2016/0299030 A1 | 10/2016 | Horbach et al. | |
| 2018/0017462 A1 * | 1/2018 | Kube | G01M 3/025 |

FOREIGN PATENT DOCUMENTS

| | | | | |
|---|---|---|---|---|
| DE | 69323121 T2 | 9/1999 | | |
| DE | 69425160 T2 | 3/2001 | | |
| DE | 102012110562 A1 | 7/2013 | | |
| DE | 102013201205 A1 | 10/2013 | | |
| DE | 102013105041 A1 | 1/2014 | | |
| DE | 102013212859 A1 | 1/2014 | | |
| DE | 102013227043 A1 | 6/2015 | | |
| EP | 854355 A1 | 7/1998 | | |
| EP | 0576243 B1 | 1/1999 | | |
| EP | 2594930 A1 * | 5/2013 | ........... | G01N 27/223 |
| EP | 2644877 A1 | 10/2013 | | |
| GB | 2256489 A * | 12/1992 | ........... | G01N 27/223 |
| WO | WO 9506881 A1 * | 3/1995 | ........... | G01N 27/223 |
| WO | 9516197 A1 | 6/1995 | | |

* cited by examiner

| Time | Current source | Measuring capacitor |
|---|---|---|
| 0 | 0 | 0 |
| 0.0001 | 5 | 1.73 |
| 0.0002 | 5 | 1.94 |
| 0.0003 | 5 | 2.02 |
| 0.0004 | 5 | 2.08 |
| 0.0005 | 5 | 2.14 |
| 0.0006 | 5 | 2.19 |
| 0.0007 | 5 | 2.25 |
| 0.0008 | 5 | 2.31 |
| 0.0009 | 5 | 2.36 |
| 0.001 | 5 | 2.42 |

| Time | Current source | Measuring capacitor |
|---|---|---|
| 0 | 0 | 0 |
| 0.0001 | 5 | 0.269 |
| 0.0002 | 5 | 0.337 |
| 0.0003 | 5 | 0.396 |
| 0.0004 | 5 | 0.454 |
| 0.0005 | 5 | 0.511 |
| 0.0006 | 5 | 0.567 |
| 0.0007 | 5 | 0.623 |
| 0.0008 | 5 | 0.678 |
| 0.0009 | 5 | 0.733 |
| 0.001 | 5 | 0.786 |

| Time | Current source | Measuring capacitor |
|---|---|---|
| 0 | 0 | 0 |
| 0.0001 | 5 | 3.99 |
| 0.0002 | 5 | 4.73 |
| 0.0003 | 5 | 4.87 |
| 0.0004 | 5 | 4.9 |
| 0.0005 | 5 | 4.9 |
| 0.0006 | 5 | 4.9 |
| 0.0007 | 5 | 4.9 |
| 0.0008 | 5 | 4.91 |
| 0.0009 | 5 | 4.91 |
| 0.001 | 5 | 4.91 |

FLUID MEASURING DEVICE AND MEASURING HEAD DEVICE FOR MOISTURE DETECTION, IN PARTICULAR IN CONTAINERS FOR FLUID-SENSITIVE ELECTRICAL AND/OR ELECTRONIC COMPONENTS IN ROAD VEHICLES

CROSS-REFERENCE TO RELATED APPLICATION

This application claims the priority, under 35 U.S.C. § 119, of German Patent Application DE 10 2016 212 986.4, filed Jul. 15, 2016; the prior application is herewith incorporated by reference in its entirety.

BACKGROUND OF THE INVENTION

Field of the Invention

The invention relates to a fluid measuring device and to a measuring head device which are suitable for a detection of moisture in sealed containers, in particular in hermetically sealed containers for electrical or electronic components in vehicles, in particular road vehicles.

Electrical or electronic components of road vehicles are usually sensitive to moisture and therefore include a sealed housing in the event of installation at a location where moisture can occur. In the case of high-voltage components, such as, for example, traction batteries or inverters of an electrical drive motor, highly specific seal-integrity requirements apply, since short circuits of those components caused by infiltrating moisture can have particularly serious consequences, for example, a vehicle fire.

The capability to detect a fluid inflow into the sealed housing is thereby highly significant in the case of electrical and/or electronic components, in particular high-voltage electrical components and/or high-voltage electronic components. Such a detection can then be provided in the form of a signal and can be communicated to a driver, for example, through a control light or an acoustic warning signal, or can also trigger other vehicle systems.

One possible source of moisture in a sealed housing in which components of a battery are located can, for example, be an outflow of cooling liquid from a housing-internal cooling system. German Patent Application DE 10 2013 105 041 A1, corresponding to U.S. Patent Application Publication US 2014/0015511, describes a sensor for detecting such a leaked cooling liquid. The sensor is part of a sensor wire, wherein one end of the wire is electrically coupled to a positive terminal or the battery and the other end of the wire is situated at a location where leaked cooling liquid can accumulate. A fault isolation detection circuit monitors a voltage output from the sensor and determines that there is a cooling liquid leak if the measured voltage potential is greater than a predefined voltage threshold value.

German Patent Application DE 10 2013 212 859 A1, corresponding to U.S. Pat. No. 8,865,333, describes a system and a method for attenuating damage of a battery in a vehicle. The system includes coolant leak sensors.

International Publication WO 9516197 A1 and German Translation DE 693 23 121 T2 of European Patent EP 0 576 243 B1, corresponding to U.S. Pat. No. 5,483,172, as well as German Patent Application DE 28 37 102 A1, corresponding to U.S. Pat. No. 4,227,151, describe a device for measuring material properties, in particular a conductivity or a dielectric constant.

German Patent Application DE 10 2013 227 043, corresponding to U.S. Patent Application Publication US 2016/0299030, A1 describes a leakage monitoring system for space-enclosing objects, for example, containers. An electrically conductive element is mounted on an enclosure wall. In order to enable simple and reliable monitoring for imminent or existing leaks even in wall regions having a large surface area, and to do so preferably universally for different types of media, the electrically conductive element is a component of a measuring bridge which includes an evaluation device for the bridge voltage and which is supplied through a voltage source with an operating voltage containing both AC voltage components as well as DC voltage components.

German Patent Application DE 10 2013 201 205 A1, corresponding to U.S. Pat. No. 9,217,690, describes a motor vehicle battery module including one or multiple battery cells and a coolant loss detection and corrective system which cooperates with the coolant and is constructed for providing temperature management of the battery module. Coolant levels in or around the battery module are detected, wherein the cooperation with a controller allows for a corrective measure in the event that a coolant leak is detected. The controller reads out a coolant level sensor which is situated in a coolant reservoir, in order to establish whether the coolant level falls below a predetermined level. If it is established that the coolant level is low, the controller signals a low-level state and implements a countermeasure. The controller has a set of activation conditions that must be met before the controller reads out the coolant level sensor.

SUMMARY OF THE INVENTION

It is accordingly an object of the invention to provide a fluid measuring device and a measuring head device for moisture detection, in particular in containers for fluid-sensitive electrical and/or electronic components in road vehicles, which overcome the hereinafore-mentioned disadvantages of the heretofore-known devices of this general type and which provide for reliable liquid and moisture detection in a sealed container or housing in order to be able to protect electronic or electrical components, in particular high-voltage components, situated in the container or housing against damage.

The invention is based on the basic concept of situating two electrodes in the sealed container, which are held in a measuring head so as to be insulated with respect to each other. These electrodes are connected to measuring head contacts on the measuring head. The measuring head contacts are connected to terminal contacts in a measuring device which has a pulsed current source and includes an evaluation circuit which, in the measuring device, monitors a measuring capacitor of an output circuit situated between the terminal contacts with respect to a state of charge. If the supply line between the measuring circuit and the measuring head is interrupted, the measuring capacitor becomes charged to a maximum state of charge of the measuring capacitor when energized with a current pulse. If there is a short circuit between the two lines that connect the terminal contacts to the measuring head contacts, the measuring capacitor does not reach a setpoint maximum state of charge when a current pulse is supplied, since the current is drained through the short circuit. If the supply lines are intact and there is no moisture in the container or housing in the interior of which the electrodes of the measuring head are situated, it is necessary, when the measuring head is energized with a measuring pulse, for the state of charge of the measuring capacitor to reach a setpoint maximum state of charge that deviates by a predefined value from the discharged state as well as from the maximum state of charge that sets-in at the measuring capacitor when a measuring head is not connected to the terminal contacts. This is achieved in that a supplementary circuit is formed in the measuring head and is connected to the measuring head contacts, the supplementary circuit establishing basic capacitance and basic resistance properties between the measuring head contacts, which correspond to those capacitance and resistance properties between the measuring head contacts that set-in in the event of a contacting with a predefined partial wetting of the at least two electrodes by using a conductive fluid having a predfined conductivity without an existence of the supplementary circuit. This offers the advantage that a fixed state of charge, namely the set point maximum state of charge, for the measuring capacitor exists and sets-in when the supply lines between the terminal contacts and the measuring head contacts are faultless and there is no moisture or liquid in the interior of the container (housing) in which the electrodes of the measuring head are situated. This set point maximum state of charge differs from the states of charge of the measuring capacitor that set-in in the event of a cable break or short circuit in the supply line or in the case of a complete absence of the measuring head. Moreover, the set point maximum state of charge also differs from the state of charge that sets in when moisture penetrates the container. In this case, the capacitance and resistance properties of the measuring head are changed, due to a conductive connection between the electrodes that is effectuated by the moisture or by the infiltrating liquid, in such a way that the maximum state of charge of the measuring capacitor that sets-in when the measuring head is energized with a current pulse is less than the setpoint maximum state of charge of the measuring capacitor.

With the foregoing and other objects in view there is provided, in accordance with the invention, a fluid measuring device for fluid-sensitive electrical and/or electronic components of road vehicles, including: a measuring head device including a measuring head which includes at least two electrodes, which are held in such a way as to be separated from each other and electrically insulated with respect to each other, wherein the measuring head includes two measuring head contacts and each of the measuring head contacts is electrically conductively connected to one of the at least two electrodes in the measuring head; and a measuring circuit including two terminal contacts, wherein each of the terminal contacts is electrically connected to one of the measuring head contacts, and wherein the measuring circuit includes a pulsed current source in order to energize, in a pulsed manner, the measuring head connected to the terminal contacts, and wherein the measuring circuit includes an output circuit between the terminal contacts including at least one measuring capacitor and an evaluation circuit for ascertaining state-of-charge information regarding the measuring capacitor in the output circuit, wherein a supplementary circuit is formed in the measuring head and is connected to the measuring head contacts and establishes basic capacitance and basic resistance properties between the measuring head contacts, which correspond to those capacitance and resistance properties between the measuring head contacts that set-in in the event of a contacting with a predefined partial wetting of the at least two electrodes by a conductive fluid having a predefined conductivity without the existence of a supplementary circuit.

With the objects of the invention in view, there is also provided a measuring head device for moisture detection in containers for fluid-sensitive electrical and/or electronic components in motor vehicles, including a measuring head including two measuring head contacts and at least two electrodes, which are held in such a way as to be separated from each other and electrically insulated with respect to each other, wherein each of the measuring head contacts is electrically connected to one of the at least two electrodes in the measuring head, wherein the measuring head contacts are connected to a supplementary circuit which establishes basic capacitance and basic resistance properties between the measuring head contacts, which correspond to those capacitance and resistance properties between the measuring head contacts that set in in the event of a contacting with a predefined partial wetting of the at least two electrodes by a conductive fluid having a predefined conductivity without an existence of a supplementary circuit.

The invention therefore provides a robust and compact moisture measuring device and a measuring head device which provide for a reliable detection of moisture in containers and simultaneously provide for a reliable detection of different fault conditions, in a simple way. In addition, it is possible to differentiate between different filling levels of an infiltrating liquid in the container.

The expression "electrodes which are held in such a way as to be separated from each other and electrically insulated with respect to each other" is understood to mean electrodes that are held in the measuring head in such a way as to be insulated with respect to the material of the measuring head and that are insulated with respect to each other, for example being separated from each other through an open space. Other embodiments can provide for a placement of an insulating material between the electrodes, which are accessible from the outside. In any case, it must be possible to establish an electrically conductive connection between the electrodes through the conductive liquid and/or moisture by partially wetting or completely wetting the electrodes, for example by dipping the electrodes into a conductive liquid. Apart from the supplementary circuit provided according to the invention, there is no electrically conductive connection between the electrodes when these electrodes are situated in a dry container or housing.

The output circuit of the measuring circuit preferably includes a series circuit made up of the measuring capacitor and a measuring resistor. This allows for a very simple construction of the output circuit at which the state of charge of the measuring capacitor is monitored through the evaluation circuit.

In one embodiment, it is provided that the evaluation circuit ascertains the state-of-charge information regarding a voltage measurement at the measuring capacitor. The voltage drop across the measuring capacitor is a measure of the state of charge of the capacitor.

Alternative embodiments can also provide that, alternatively, a voltage drop is measured across the measuring resistor, which is situated in series with the measuring capacitor. Other embodiments can ascertain the state of charge through a current measurement, which is carried out in the series connection with the measuring capacitor, in particular through an integrating current measurement. A voltage measurement, however, is particularly simple and robust and, therefore, is preferred.

The measuring capacitor, the measuring resistor, and the current pulse generated by the current source are preferably matched to each other and are dimensioned in such a way that a set point maximum state of charge of the measuring capacitor resulting upon an energization, with a current pulse, of the measuring head which is connected to the terminal contacts and the electrodes of which are situated in a moisture-free container, differs from the discharged state of the measuring capacitor by a predefined minimum value, wherein the predefined minimum value is less than a difference between the discharged state and a maximum state of charge of the measuring capacitor that sets -n in the case of a current pulse of the measuring circuit when the measuring head is not connected to the terminal contacts of the measuring circuit. This maximum state of charge also sets-in when the supply line to the measuring head is interrupted. The ratio between the maximum state of charge, which sets-in without the existence of the measuring head, and the maximum setpoint maximum state of charge can be freely selected, and is preferably between 10% and 90% of the maximum state of charge, more preferably between 30% and 80% of the maximum state of charge and, most preferably, 50% to 80% of the maximum state of charge.

On one hand, it is ensured through the selection that the fault conditions of short circuit, absence of a measuring head, or damage of the supply line are reliably differentiated from the "normal" operating state in which no moisture or liquid has penetrated the container or, on the other hand, from the state in which a change in the capacitance and resistance properties of the measuring head caused by moisture or liquid has occurred.

In one preferred embodiment, it is provided that the evaluation device is constructed for outputting an alarm signal depending on the state-of-charge information regarding the measuring capacitor. It is preferred to output an alarm signal when the ascertained maximum state of charge upon energization with a current pulse deviates from the set point maximum state of charge of the measuring capacitor by more than a predefined alarm tolerance value. This always occurs when moisture has penetrated the container, a short circuit has occurred in the supply line or the measuring head, or a line interruption of the supply line has occurred, or the measuring head is completely missing.

In one refinement, the evaluation device is constructed in such a way that different alarm signals are output for the different fault conditions or the different fault conditions are coded in the alarm signal. As a result, troubleshooting is substantially simplified for a user. Furthermore, it is possible to configure the alarm signal—which indicates that moisture has penetrated the container in which the electrodes of the measuring head are situated—or to configure the error coding in such a way that these are a measure of the quantity of moisture that has penetrated the container. Depending on this measure, it is then possible to carry out a different reaction, which may be stepped, possibly with the aid of a control system of the vehicle. These different reactions can be the display of an interference signal, a display of a fatal fault, an initiation of technical measures for switching off the high-voltage components in the container, an initiation of fireproofing measures, etc.

The supplementary circuit in the measuring head is preferably constructed as a series circuit of passive components. This offers the advantage that the measuring head is robust and can be reliably operated even in extreme environmental conditions.

Particularly preferably, the supplementary circuit is constructed as a network which includes a series circuit made up of a series resistor and a capacitor in parallel to a load resistor. Such a circuit best depicts the behavior of a measuring head which includes only two electrodes, which are held in such a way as to be insulated with respect to each other, and does not include a supplementary circuit and the electrodes of which are conductively contacted to a conductive liquid, e.g., in that there is a predefined partial wetting of the electrodes. The specific resistance and capacitance properties of the supplementary circuit can be varied within broad limits, but should be selected in such a way that a maximum state of charge of the measuring capacitor results in the measuring circuit shared with the measuring head device, the maximum state of charge substantially differing from a discharged state of charge and from a maximum state of charge that occurs in the event of a current pulse and the absence of a measuring head. The maximum state of charge that occurs is considered to be a set point maximum state of charge. This means that the supplementary circuit must not result in a "short circuit" between the two electrodes, but rather must still provide a high ohmic resistance to DC voltages and, on the other hand, increases a capacitance of the measuring head device, but which is configured in such a way that a notable charging of the measuring capacitor of the output circuit nevertheless takes place, and therefore the set point maximum state of charge differs substantially from the discharged state of the measuring capacitor in the measuring device and from a maximum possible state of charge occurring in the event of a current pulse.

A robustness of the measuring head or the measuring head device can be increased by casting the components of the supplementary circuit into the measuring head material. As a result, an optimal insulation and optimal protection against mechanical as well as chemical damage of the components of the supplementary circuit and, therefore, of the entire supplementary circuit, is ensured.

Particularly preferably, the measuring head is constructed as a closure device. A closure device is considered to be any device which can close a container or an opening in a container.

One preferred embodiment provides that the measuring head is constructed as a threaded closure or a bayonet closure or a flange having a sealing surface. Preferably, the closure device is round, in particular circular, which is advantageous in the case of threaded connections, bayonet closures, and in a closure device constructed as a type of flange. The advantage of threaded or bayonet closure devices is that no additional fastening devices are required in order to fasten the measuring head in a corresponding opening constructed for accommodating a threaded closure or a bayonet closure. If the closure device is constructed as a flange, then, for example, a clamping ring can be utilized as a fastening element, or one or multiple clamps can be utilized, which may also be already fastened on the measuring head.

The energization with the current source preferably takes place in such a way that its current-pulse duration is shorter, by at least one order of magnitude, than an interval to a current pulse generated at a subsequent point in time. As a result, it is ensured that the maximum state of charge ascertained at the measuring capacitor is induced by only one current pulse in each case.

Preferably, a ratio of current pulse duration to a current pulse interval has a value in the range of 1:10 to 1:10,000, more preferably of 1:50 to 1:1,000, and most preferably between 1:90 and 1:110. Given these values, moreover, an output utilized for measuring the moisture or dryness in the container is adequately reduced.

In order to be able to react sufficiently quickly to an infiltration by moisture, current pulse repetition frequencies in the range between 10 Hz and 100 kHz, preferably in the range between 10 Hz and 10 kHz, most preferably in the range between 900 Hz and 1,100 Hz are utilized. It is possible to generate the current pulses at variable points in time, although it is preferred to generate the current pulses periodically.

In principle, it is also possible to utilize a pulsating, rectified AC voltage or even an AC voltage.

In order to achieve redundancy, it is provided in some embodiments that the measuring head includes, in addition to the at least two electrodes, two further electrodes which are held in an individually insulated manner. One further supplementary circuit can be provided between these electrodes. In addition, one further redundant measuring circuit for the further electrodes of the measuring head can be provided. Alternatively, the further electrodes can also be connected in pairs to the at least two electrodes in the measuring head which then includes only one supplementary circuit which may have been modified in terms of the construction. As a result, the sensitivity of the measuring head to moisture penetration into the container can be increased.

Other features which are considered as characteristic for the invention are set forth in the appended claims.

Although the invention is illustrated and described herein as embodied in a fluid measuring device and a measuring head device for moisture detection, in particular in containers for fluid-sensitive electrical and/or electronic components in road vehicles, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
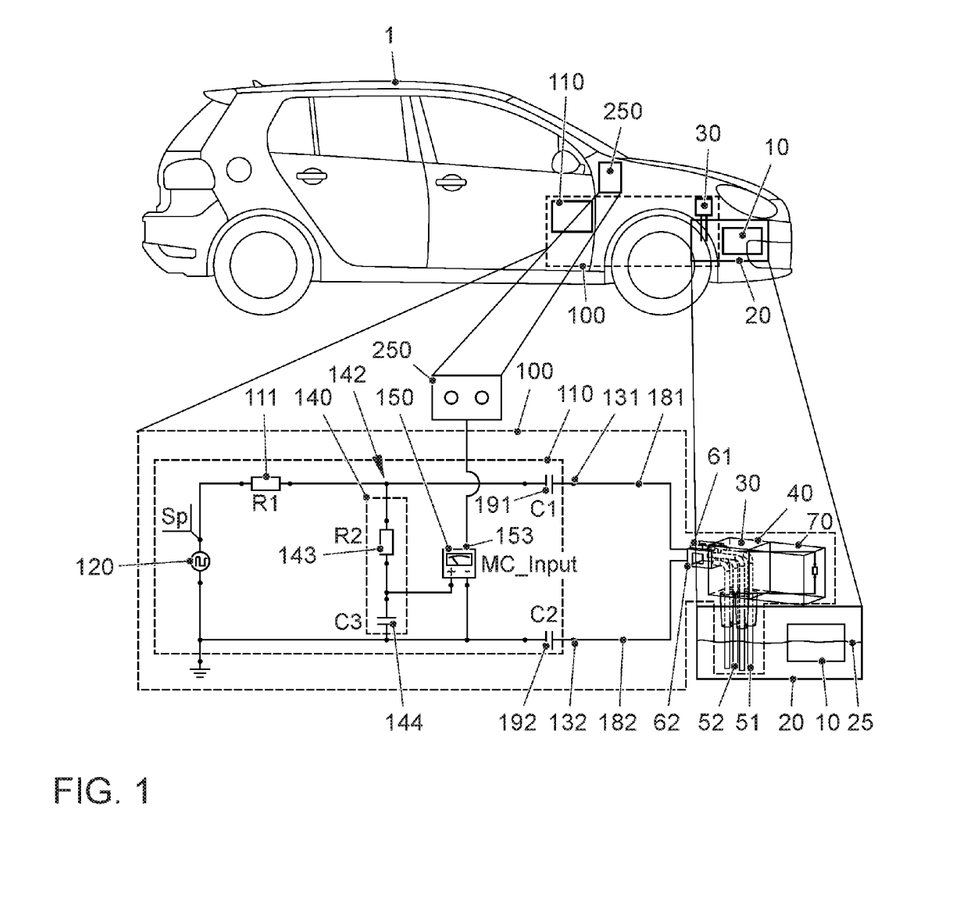
FIG. 1 is a diagrammatic, side-elevational view of a motor vehicle including a schematic circuit diagram of a fluid measuring device and a measuring head device.

Referring now to the figures of the drawings in detail and first, particularly, to FIG. 1 thereof, there is seen a diagrammatic and schematic representation of a motor vehicle 1 which includes a high-voltage component 10 which is constructed, for example, as a traction battery. A traction battery is generally situated between the axles of the motor vehicle 1. For the sake of clarity, the high-voltage component 10, which does not necessarily need to be a traction battery, but rather can be any other type of high-voltage-carrying element, is shown as being situated in the engine compartment. The high-voltage component 10 is enclosed in a container 20 which is also referred to as a housing and is sealed with respect to moisture and liquids. In the normal state, there is no free moisture or free liquid in the container 20. Fluid in a sealed system, for example cooling liquid in a closed and sealed cooling system of the high-voltage component, can be located in the container 20, however. A measuring head device 30 is situated at the container 20 or housing. This measuring head device is a component of a fluid measuring device 100. In addition to the measuring head device 30, the fluid measuring device 100 includes a measuring circuit 110 and lines 181, 182. These lines connect terminal contacts 131, 132 of the measuring circuit 110 to measuring head contacts 61, 62 of the measuring head device 30.

The measuring head device 30 includes a measuring head 40 in which at least two electrodes 51, 52 are held in such a way as to be insulated with respect to each other. The electrodes 51, 52 extend into the sealed container 20. Each of the at least two electrodes 51, 52 is electrically conductively connected to one of the measuring head contacts 61, 62. If a liquid 25 penetrates the container 20, a conductive connection between the at least two electrodes 51, 52 is formed through this liquid. The liquid 25 can penetrate the container from the outside or can flow out of the high-voltage component or a component thereof, for example, a cooling system, and penetrate the container 20 in this way. The measuring circuit 110 detects this change in the capacitance and resistance properties of the measuring head device 30 or of the measuring head 40.

For this purpose, the measuring circuit 110 has a current source 120 which is preferably constructed as a pulsed current source. The measuring circuit 110 further includes an output circuit 140 which is situated between the terminal contacts 131, 132 and includes a measuring capacitor 144. Furthermore, an evaluation circuit 150 is provided, which monitors a state of charge of the measuring capacitor 144. If the measuring head device 30 is energized in a pulsed manner by using the current source 120, the charging behavior of the measuring capacitor 144 in the output circuit 140 of the measuring device 110 is dependent on the resistance and capacitance properties of the measuring head device 30, for example due to a change in the conductivity between the two electrodes 51, 52 as a result of a liquid 25 having penetrated the container 20. A schematic equivalent circuit diagram for the measuring circuit 110 is represented in FIG. 1. It is clear to a person skilled in the art that the measuring circuit can have a substantially more complex construction overall, but the important components are shown in the equivalent circuit diagram.

In the normal operating state, there is no fluid 25 in the container 20. Therefore, no electrical conductance takes place between the electrodes 51, 52 through the liquid. In order to be able to nevertheless differentiate this normal operating state from a fault condition in which, for example, one of the lines 181, 182 is interrupted, the measuring head device 30 or the measuring head 40 includes a supplementary circuit 70. This supplementary circuit 70 is preferably constructed as a network 71 made up of passive electronic components. The supplementary circuit 70 is constructed in this way and is situated between the measuring head contacts 61, 62 and the electrodes 51, 52 of the measuring head 40, and is connected thereto, and therefore resistance and capacitance properties are provided to the measuring circuit 110, which are of the type that would occur at a measuring head 40 that does not include this supplementary circuit, although the container has a predefined filling level with a conductive liquid, e.g., a sodium chloride solution, a water-glycol mixture, etc. This is equivalent to the case in which a partial wetting of the at least two electrodes is carried out through a conductive liquid having a predefined conductivity, and a contacting thereby takes place. As a result, it is possible for the measuring circuit 110 to differentiate the normal state from a fault condition, in which the measuring head 40 is not connected or one of the lines 181, 182 is interrupted or one of the electrodes 51, 52 in the measuring head 40 is broken or the supplementary circuit 70 is defective.

Figure 2:
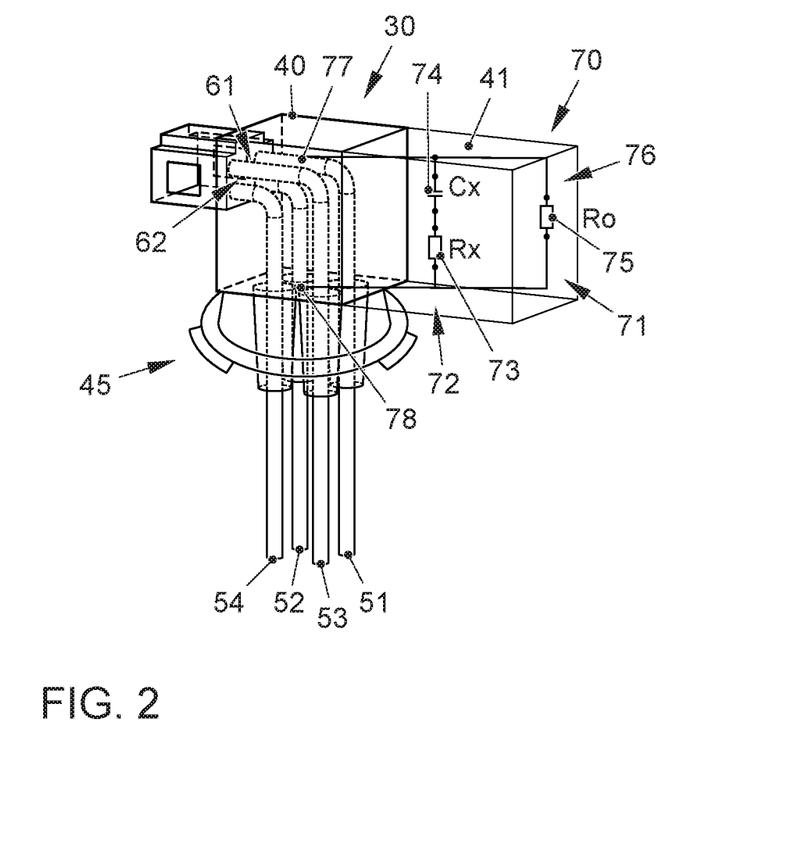
FIG. 2 is a perspective view of a measuring head device.

The measuring head device 30 is diagrammatically represented in FIG. 2. Identical technical features are provided with the same reference numbers in all figures. Only the differing features are described in the different figures, however. The measuring head device 30 includes a measuring head 40 made of a measuring head material 41 which is preferably insulating. Alternatively or additionally, an insulating material can be situated around the electrodes 51, 52 and in which the electrodes are held in the measuring head in such a way as to be insulated with respect to each other. Furthermore, the supplementary circuit 70, which includes a network 71 of preferably passive components, is situated in the measuring head 40. In the preferred embodiment, the network 71 includes a series circuit 72 made up of a resistor 73 and a capacitor 74 which is connected in parallel to a load resistor 75. The supplementary circuit 70 is a two-terminal network 76, one pole 77 of which is electrically conductively connected to the electrode 51 and the other pole 78 of which is electrically conductively connected to the other electrode 52, or its one pole 77 is connected to a measuring head contact 61 and its other pole 78 is connected to the other measuring head contact 62. The components of the supplementary circuit 70 and, therefore, the entire supplementary circuit 70 are preferably cast into the measuring head material 41 or another insulating material. In this way, the supplementary circuit 70 and the components are well protected mechanically as well as chemically as well as against other environmental influences.

Preferably, the measuring head 40 is constructed as a closure device 45, for example as a bayonet closure, a threaded closure, or a sealing flange having a sealing surface. This offers the advantage that the measuring head device 30 or the measuring head 40 can be easily inserted into the container and exchanged, while nevertheless ensuring that a reliable and simple sealing of the container is possible. A sealing device, for example, a polymer ring or the like, is preferably situated between the container and the closure device. Alternatively, the measuring head device can also be integrally integrated into the container or a container wall.

Figure 3A:
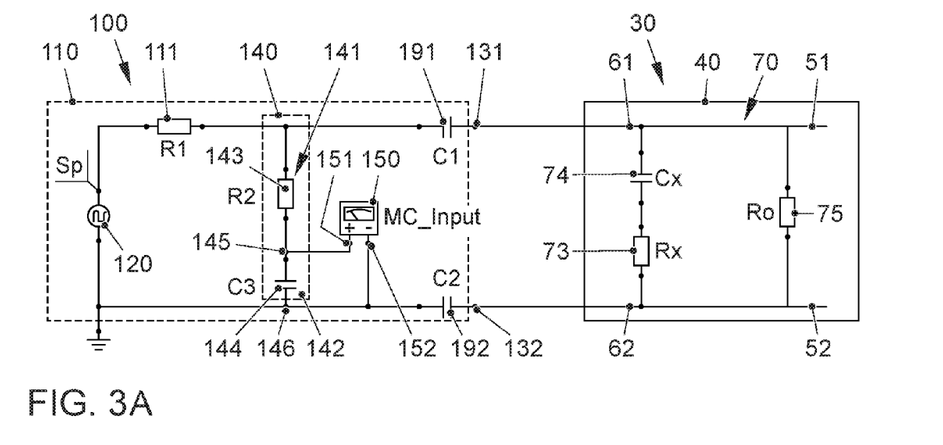
FIG. 3A is a schematic wiring diagram of a measuring device including a measuring head device.

A schematic equivalent diagram of the fluid measuring device 100 is represented in FIG. 3A. The output circuit 140 includes a circuit network 141 which includes a series circuit 142 of a measuring resistor 143 and a measuring capacitor 144. The output circuit is situated in parallel to the terminal contacts 131, 132 in the measuring circuit 110. An internal resistor 111 limits the current of the current pulses output by the measuring circuit 110.

The lines 181, 182 are preferably capacitatively coupled to the measuring circuit with the aid of terminal capacitors 191, 192 which are formed upstream from the terminal contacts 131, 132. The terminal capacitors 191, 192 can ensure that a common-mode component of the current source 120 does not influence the measurement. Furthermore, the terminal capacitors 191, 192 offer protection against electrostatic discharge (ESD protection) during the handling of the measuring circuit 110. If the voltage at the output of the current source 120 varies between zero and the maximum voltage, and therefore does not have a common-mode component, and ESD protection is dispensed with, the terminal capacitors 191, 192 can also be dispensed with.

The one measurement input 151 of the evaluation circuit 150 is connected to the center tap 145 of the series circuit 142. A reference terminal 152 is connected to the other pole 146 of the measuring capacitor 144. Preferably, the evaluation circuit 150 is a voltage measuring circuit which evaluates a voltage that drops across the measuring capacitor 144. In the case of a capacitor, the voltage drop is a measure of the state of charge of the capacitor.

The supplementary circuit 70 for the measuring head device 30 that results is identical to the supplementary circuit 70 formed between the electrodes in the measuring head.

Figure 3B:
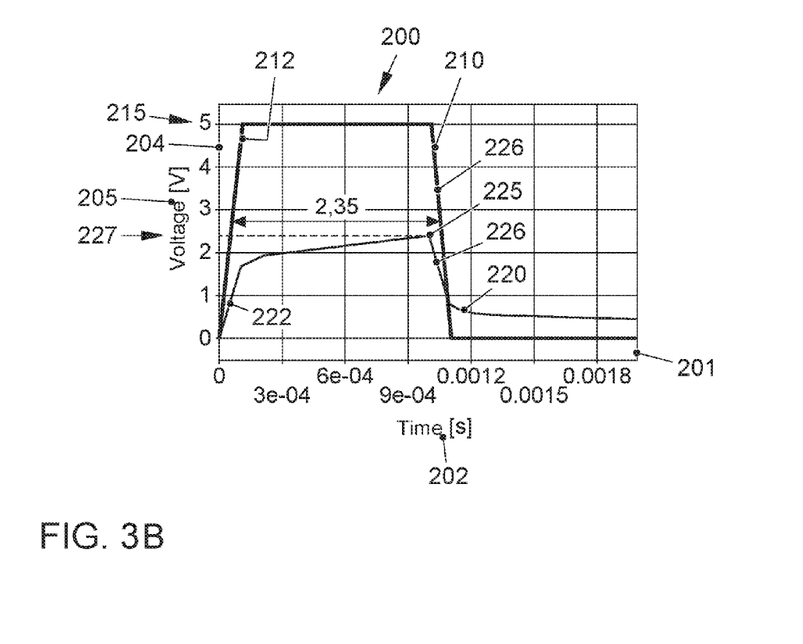
FIG. 3B is a voltage-time diagram, measured at a measuring capacitor.

A voltage-time diagram 200 is represented in FIG. 3B. The time axis 202 is formed on the x-axis 201 and the voltage 205 is indicated on the y-axis 204. In the voltage-time diagram 200, the voltage progression 210 at the current source is shown, on one hand, and the voltage progression 220 at the measuring capacitor is shown, on the other hand. The voltage progression 220 at the measuring capacitor is equal to the voltage progression that the evaluation circuit evaluates in order to monitor the state of charge of the measuring capacitor. A person skilled in the art understands that the monitoring of the state of charge of the capacitor can also be carried out by monitoring voltage at the measuring capacitor. An equivalent thereto would be monitoring voltage at the measuring resistor. Alternatively, a current measuring device could be situated between the measuring resistor and the measuring capacitor, which ascertains the state of charge of the capacitor on the basis of a current measurement, in particular an integrated current measurement. Preferably, however, an evaluation circuit 150 is provided, as is shown herein in all exemplary embodiments, which carries out a voltage evaluation.

It is clearly evident that, when a current pulse is generated, a rapid voltage increase 212 to a maximum voltage 215 takes place at the voltage source and, after a time period 235 which is basically identical to one current pulse time period, a voltage drop to 0 V takes place. At the measuring capacitor, the voltage course 220 likewise exhibits a voltage increase 222 which exhibits a maximum voltage 225 at the end of the current pulse. After the end of the current pulse, a voltage drop 226 is likewise observed in the voltage progression 220 at the measuring capacitor. This takes place in a substantially delayed manner, however. On the basis of the voltage progression or the state of charge of the measuring capacitor, which is represented in the voltage-time diagram 200 according to FIG. 3B, it is possible to infer the correct mode of operation of the fluid measuring device 100 or the complete reliability of the measuring head device 30. If the maximum voltage 225 matches a predefined setpoint maximum state of charge 227 or a set point maximum voltage equivalent thereto, it is ensured, on one hand, that there is no short circuit or cable break in the supply lines and, on the other hand, that no liquid has penetrated the container.

Figure 3C:
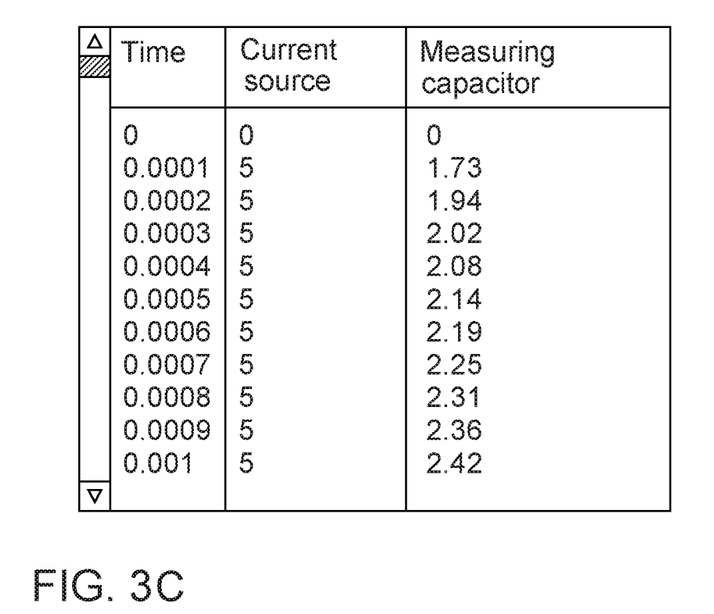
FIG. 3C is a measured value table.
Figure 3D:
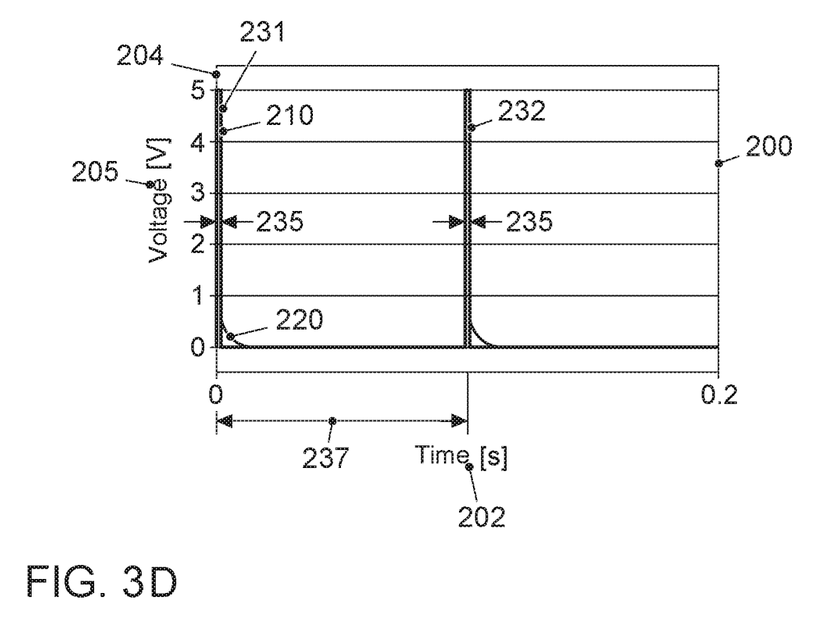
FIG. 3D is a further voltage-time diagram which is similar to that in FIG. 3B, but with a different time resolution.

A table is indicated in FIG. 3C, which includes measured values for the voltages at the current source and at the measuring capacitor during the time period of the current pulse. In the embodiment represented, the set point maximum voltage 227 reaches a value of approximately one-half the voltage that is generated at the current source. It is apparent from FIG. 3D that the current source is operated preferably in a pulsed manner, in such a way that a time period 235 or pulse duration is substantially shorter than a time interval 237 between two consecutive voltage pulses 231, 232 which correspond to the generated current pulses. For example, the time period 235 of a pulse 231 is one one-hundredth of the time interval between the pulses, for example measured at the point at which the voltage starts to increase in each case. The current pulse lasts for one unit of time, for example. The current subsequently remains at zero for 99 units of time. A repetition frequency between the individual current pulses can be selected in the range between 10 Hz and 100 kHz, preferably on the order of 1,000 Hz.

Figure 4A:
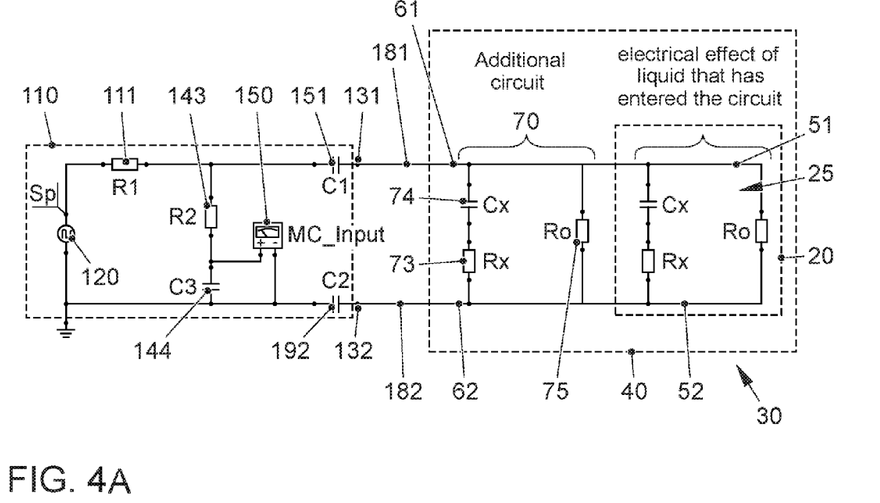
FIG. 4A is a schematic equivalent circuit diagram of the fluid measuring device including a measuring head device which is situated in a container into which a liquid has penetrated.
Figure 4B:
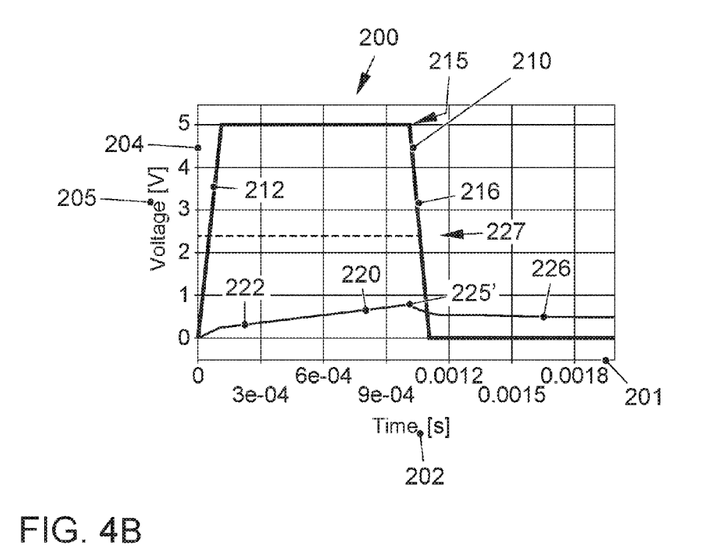
FIG. 4B is a voltage-time diagram corresponding to the equivalent circuit diagram according to FIG. 4A.
Figure 4C:
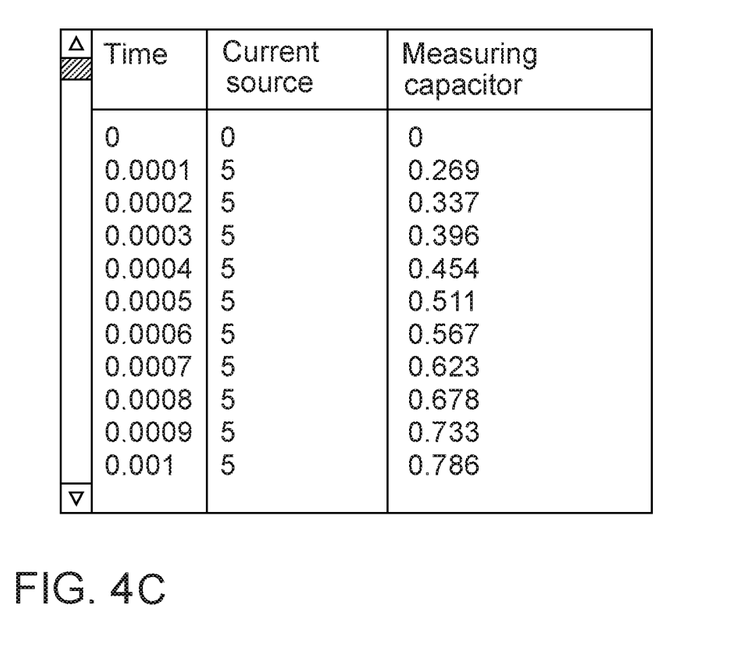
FIG. 4C is a table of measured values corresponding to that in FIG. 4B.

FIGS. 4A to 4C, which correspond to FIGS. 3A to 3C, are intended to explain how the voltage progression at the measuring capacitor 144 changes when liquid 25 penetrates the container 20. This penetrating liquid 25 changes the resistance and capacitance properties of the measuring head device 30. This is indicated in the area on the right in the equivalent circuit diagram of FIG. 4A by using an additional circuit network 80 which is also referred to as a fluid circuit network. As is evident from FIG. 4B, the voltage progression 210 at the current source 120 does not change as compared to the side view in FIGS. 3A to 3D. The voltage progression 220 at the measuring capacitor 144 differs from the voltage progression 220 in FIG. 3B, however, in that the maximum voltage 225' reached in FIG. 4B has a substantially lower value than the set point maximum voltage 227.

Therefore, if the ascertained maximum voltage, which indicates the maximum state of charge during the current pulse, deviates from the set point maximum voltage 227 by more than an alarm tolerance value 228, as shown in FIG. 4B, the evaluation circuit 150 generates an alarm signal preferably at a signal output 153. This signal can be constructed to be analog or digital and can be analog or digitally encoded, in order to permit different fault conditions to be signaled.

As is evident in FIG. 1, the signal output 153 is preferably connected to a display device 250 which can, for example, be a central control field display or a multifunctional operating device in the motor vehicle. Due to triggered by the alarm signal, it is possible, for example, for the activation of a warning light or the like to be triggered. The alarm signal can also be evaluated and utilized by further control devices. FIG. 4C shows a table, which is similar to that in FIG. 3C, of the voltage values—corresponding to FIG. 4B—for the voltage progression 210 at the current source 120 and at the measuring capacitor 144 during the current pulse.

Figure 5A:
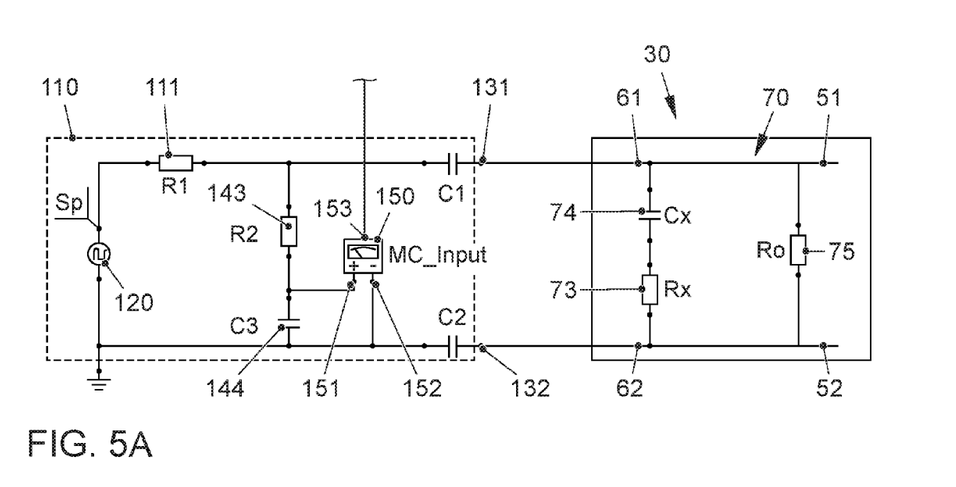
FIG. 5A is an equivalent circuit diagram of a moisture measuring device in which the supplementary circuit of the measuring head device is defective or a supply line is broken.
Figure 5B:
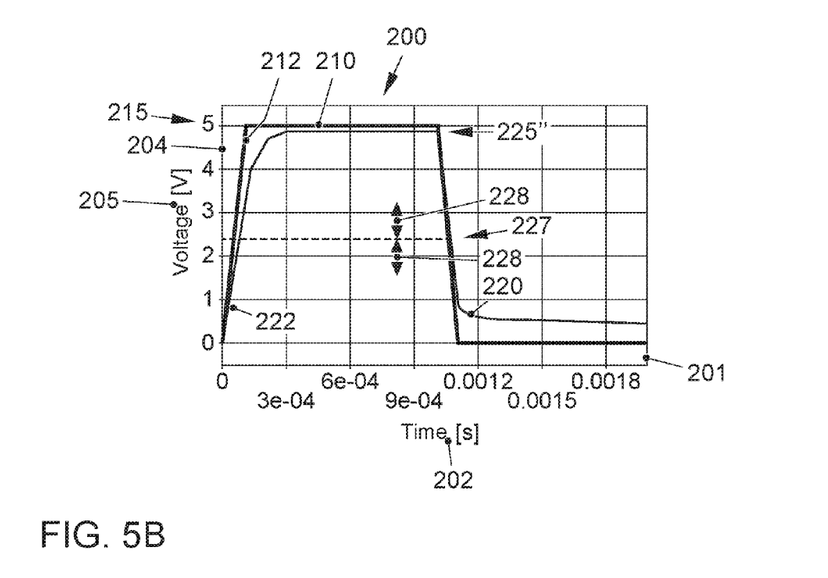
FIG. 5B is a voltage-time diagram corresponding to the equivalent circuit diagram in FIG. 5A.
Figure 5C:
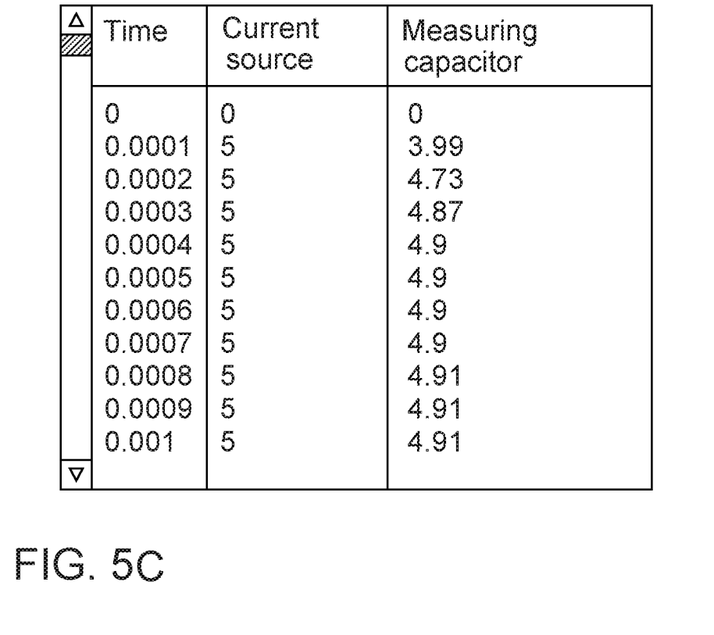
FIG. 5C is a measured value table corresponding to the diagram in FIG. 5B.
Figure 5D:
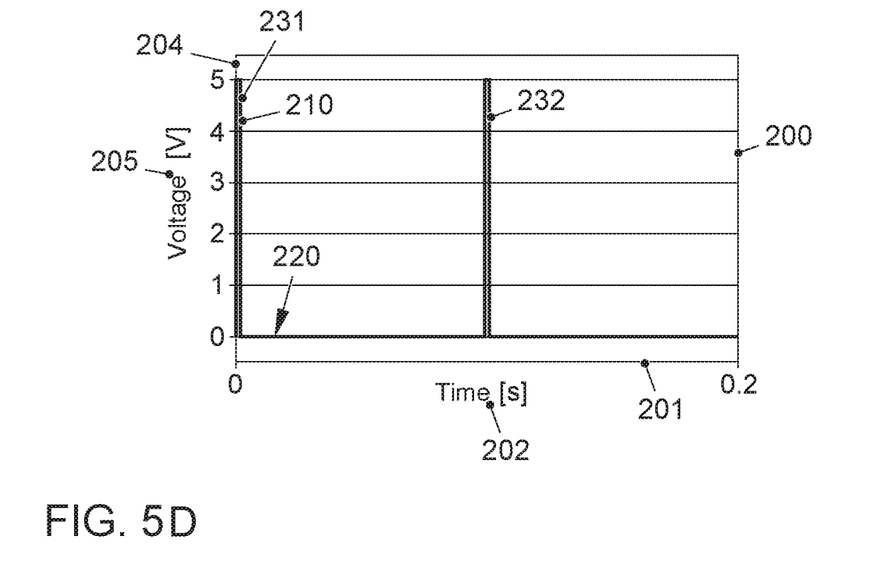
FIG. 5D is a voltage-time diagram for a longer period of time, corresponding to the equivalent circuit diagram according to FIG. 5A.

Schematically represented in FIG. 5A is a schematic circuit which schematically represents a cable break in one of the supply lines 181. A similar behavior is exhibited when the supplementary circuit is defective. FIGS. 5B to 5D show the corresponding voltage-time diagrams and the value table of the voltage progressions similarly to those in FIGS. 3A to 3D. In FIG. 5B, it is clearly evident that, in this case, the maximum voltage 225" at the measuring capacitor 144 approximately corresponds to the maximum voltage 215 at the current source. In any case, it is substantially greater than the set point maximum voltage 227. This fault is therefore to be clearly differentiated from the normal operating state and also from the state in which liquid 25 has penetrated the sealed container 20. As is apparent from FIG. 4D, the discharging of the measuring capacitor 144 also takes place much more rapidly than in the situation with the intact measuring head 40.

In the case of the further fault, in which a short circuit occurs between the supply lines 181, 182 or in the measuring head 40, for example, in the supplementary circuit, or if the electrodes are bent, during maintenance, for example, so that the electrodes contact one another, there is no charging or hardly any charging of the measuring capacitor 144.

Depending on the change in the conductive connection between the electrodes 51, 52 established through liquid or moisture, the maximum voltage ascertained at the measuring capacitor therefore drops, the better the electrical conductivity is between the electrodes. As soon as a predefined quantity of liquid has penetrated the container 20 and has resulted in a wetting or partial wetting of the electrodes, a deviation from the set point maximum voltage or the set point state of charge can therefore be reliably ascertained and an alarm signal can be generated.

Only two electrodes of the measuring head were used in all of the above-described embodiments. Embodiments are possible, however, as schematically represented in FIG. 1 and FIG. 2, in which the measuring head also includes more electrodes, for example, four electrodes, specifically further electrodes 53 and 54 in addition to the at least two electrodes 51 and 52. These embodiments can include a separate supplementary circuit in order to build up a redundancy or can be operated without a supplementary circuit preferably at a further measuring circuit. A switchover device in the measuring device is also conceivable, which connects different electrode pairs of a measuring head to the output circuit one after the other, for example, in alternation, and therefore evaluates different electrode pairs in alternation. Other embodiments can provide that the further electrodes are contacted in parallel to the at least two electrodes 51, 52.

In order to dimension the values of the components of the supplementary circuit, the electrodes of a measuring head at which the supplementary circuit has not yet been formed can be dipped into a conductive fluid, for example a mixture of 50% glycol and 50% water or a sodium chloride solution, so that each of the electrodes is wetted by a predefined percentage, for example 50%. The resistance and capacitance properties are then measured by this measuring head, and the components of the supplementary circuit are therefore established in such a way that the measuring head including the supplementary circuit exhibits the same resistance and capacitance properties when the electrodes are located in a dry, liquid-free container.

The following is a summary list of reference numerals and the corresponding structure used in the above description of the invention:

LIST OF REFERENCE NUMBERS 1 motor vehicle
10 high voltage component (e.g., traction battery)

20 container (housing)
25 liquid
30 measuring head device
40 measuring head
41 measuring head material
45 closure device
51, 52 electrodes
55, 56 further electrodes
61, 62 measuring head contacts
70 supplementary circuit
71 network
72 series circuit
73 resistor
74 capacitor
75 load resistor
76 two-terminal network
77 pole
79 other pole
80 additional circuit network
100 fluid measuring device
110 measuring circuit
111 internal resistor
120 current source (pulsed)
131, 132 terminal contact
140 output circuit
141 circuit network
142 series circuit
143 measuring resistor
144 measuring capacitor
145 center tap
146 other pole
150 evaluation circuit
151 measurement input
152 reference terminal
153 signal output
171, 172 coupling capacitor
181, 182 line
191, 192 terminal capacitors
200 voltage-time diagram
201 x-axis
202 time axis
204 y-axis
205 voltage
210 voltage progression at the current source
211 voltage pulse
212 voltage increase
215 maximum voltage
216 voltage drop
220 voltage progression at the measuring capacitor
221 voltage pulse
222 voltage increase
225 maximum voltage
226 voltage drop
227 set point maximum voltage
228 alarm tolerance value
231, 232 pulse
235 time period
237 time interval
250 display device

The invention claimed is:

1. A fluid measuring device for at least one of fluid-sensitive electrical or electronic components of road vehicles, the fluid measuring device comprising:
a measuring head device having a measuring head including at least two electrodes being held in such a way as to be separated from each other and electrically insulated with respect to each other, said measuring head including two measuring head contacts each being electrically conductively connected to a respective one of said at least two electrodes in said measuring head;
a measuring circuit including two terminal contacts, each of said terminal contacts being electrically connected to a respective one of said measuring head contacts, said measuring circuit including a pulsed current source for pulsed energizing of said measuring head connected to said terminal contacts, and said measuring circuit including an output circuit connected between said terminal contacts and having at least one measuring capacitor and an evaluation circuit for ascertaining state-of-charge information regarding said measuring capacitor in said output circuit; and
a supplementary circuit formed in said measuring head, connected to said measuring head contacts and establishing basic capacitance and basic resistance properties between said measuring head contacts corresponding to capacitance and resistance properties between said measuring head contacts setting-in in an event of contact occurring with a predefined partial wetting of said at least two electrodes caused by a conductive fluid having a predefined conductivity without an existence of said supplementary circuit.

2. The device according to claim 1, wherein said output circuit includes a series circuit of said at least one measuring capacitor and an ohmic measuring resistor.

3. The device according to claim 2, which further comprises: a moisture-free container containing said electrodes of said measuring head;
said at least one measuring capacitor, said measuring resistor and a current pulse generated by said current source being matched to each other and dimensioned in such a way that a setpoint maximum state of charge of said at least one measuring capacitor resulting upon an energization, with a current pulse, of said measuring head being connected to said terminal contacts differs from a discharged state of said at least one measuring capacitor by a predefined minimum value; and
the predefined minimum value being less than a difference between the discharged state and the maximum state of charge of said at least one measuring capacitor setting-in upon a current pulse of said measuring circuit when said measuring head is not connected to said terminal contacts of said measuring circuit.

4. The device according to claim 3, wherein said evaluation device is configured for outputting an alarm signal when the ascertained maximum state of charge upon energization with a current pulse deviates from the setpoint maximum state of charge of said measuring capacitor by more than a predefined alarm tolerance value.

5. The device according to claim 1, wherein said supplementary circuit is a series circuit of passive components.

6. The device according to claim 1, wherein said supplementary circuit includes a network of a series circuit of a series resistor and a capacitor connected in parallel with a load resistor.

7. The device according to claim 1, which further comprises a measuring head material, said supplementary circuit being cast into said measuring head material.

8. The device according to claim 1, wherein said measuring head is constructed as a closure device.

9. The device according to claim 8, wherein said closure device is constructed as a threaded connection or a bayonet connection or a flange including a sealing surface.

* * * * *